(12) United States Patent
Al-Daous et al.

(10) Patent No.: US 11,338,269 B2
(45) Date of Patent: May 24, 2022

(54) CATALYTIC HYDROCARBON DEHYDROGENATION

(71) Applicant: Saudi Arabian Oil Company, Dhahran (SA)

(72) Inventors: Mohammed Abdulmajeed Al-Daous, Thuwal (SA); Hussam A. Bahlouli, Thuwa (SA)

(73) Assignee: Saudi Arabian Oil Company, Dhahran (SA)

( * ) Notice: Subject to any disclaimer, the term of this patent is extended or adjusted under 35 U.S.C. 154(b) by 175 days.

(21) Appl. No.: 16/566,778

(22) Filed: Sep. 10, 2019

(65) Prior Publication Data

US 2021/0069677 A1 Mar. 11, 2021

(51) Int. Cl.
| | | |
|---|---|---|
| *B01J 23/62* | (2006.01) | |
| *B01J 21/06* | (2006.01) | |
| *B01J 23/58* | (2006.01) | |
| *B01J 21/04* | (2006.01) | |
| *B01J 23/04* | (2006.01) | |
| *B01J 23/14* | (2006.01) | |
| *B01J 23/42* | (2006.01) | |
| *B01J 37/08* | (2006.01) | |
| *B01J 37/14* | (2006.01) | |
| *B01J 37/16* | (2006.01) | |
| *C07C 5/32* | (2006.01) | |

(52) U.S. Cl.
CPC ............. *B01J 21/066* (2013.01); *B01J 21/04* (2013.01); *B01J 23/04* (2013.01); *B01J 23/14* (2013.01); *B01J 23/42* (2013.01); *B01J 23/58* (2013.01); *B01J 23/626* (2013.01); *B01J 37/08* (2013.01); *B01J 37/14* (2013.01); *B01J 37/16* (2013.01); *C07C 5/325* (2013.01)

(58) Field of Classification Search
CPC ........ B01J 21/04; B01J 21/066; B01J 23/626; B01J 23/58
See application file for complete search history.

(56) References Cited

U.S. PATENT DOCUMENTS

| | | | |
|---|---|---|---|
| 2,328,754 | A | 9/1943 | Thomas |
| 2,620,293 | A | 12/1952 | Blue et al. |

(Continued)

FOREIGN PATENT DOCUMENTS

| | | |
|---|---|---|
| JP | 2006198616 | 8/2006 |
| WO | 2010133565 | 11/2010 |

OTHER PUBLICATIONS

PCT International Search Report and Written Opinion in International Application No. PCT/US2020/050,109, dated Dec. 22, 2020, 13 pages.

(Continued)

*Primary Examiner* — Jun Li
(74) *Attorney, Agent, or Firm* — Fish & Richardson P.C.

(57) ABSTRACT

A catalyst for dehydrogenation of hydrocarbons includes a support including zirconium oxide and alumina. A concentration of the zirconium oxide in the catalyst is in a range of from 1 weight percent (wt. %) to 20 wt. %. The catalyst includes from 0.01 wt. % to 2 wt. % of an alkali metal or alkaline earth metal. The catalyst includes from 1 wt. % to 2 wt. % of tin. The catalyst includes from 0.1 wt. % to 2 wt. % of a platinum group metal. The alkali metal or alkaline earth metal, tin, and platinum group metal are disposed on the support.

20 Claims, 4 Drawing Sheets

(56) References Cited

U.S. PATENT DOCUMENTS

| | | | |
|---|---|---|---|
| 3,531,543 | A | 9/1970 | Clippinger et al. |
| 3,745,112 | A | 7/1973 | Rausch |
| 3,892,657 | A | 7/1975 | Wilhelm |
| 3,909,451 | A | 9/1975 | Wilhelm |
| 4,055,513 | A | 10/1977 | Wheelock |
| 4,101,593 | A | 7/1978 | Hayes et al. |
| 4,210,769 | A | 7/1980 | Antos |
| 4,329,258 | A | 5/1982 | Engelhard et al. |
| 4,358,397 | A | 11/1982 | Chu |
| 4,363,721 | A | 12/1982 | Engelhard et al. |
| 4,438,288 | A | 3/1984 | Imai et al. |
| 4,458,098 | A | 7/1984 | Antos |
| 4,552,855 | A | 11/1985 | Ozin et al. |
| 4,585,897 | A | 4/1986 | Fields et al. |
| 4,677,237 | A | 6/1987 | Imai et al. |
| 4,827,072 | A | 5/1989 | Imai et al. |
| 4,914,075 | A * | 4/1990 | Bricker .............. C07C 5/3337 502/328 |
| 5,453,558 | A | 9/1995 | Alexander et al. |
| 5,482,910 | A | 1/1996 | Bricker et al. |
| 5,486,348 | A | 1/1996 | Verduijn et al. |
| 5,736,478 | A | 4/1998 | Cortright et al. |
| 6,218,328 | B1 | 4/2001 | Wu et al. |
| 6,566,573 | B1 | 5/2003 | Bharadwaj et al. |
| 8,404,104 | B2 | 3/2013 | Pan et al. |
| 11,097,257 | B2 * | 8/2021 | Al-Daous .............. B01J 29/62 |
| 2005/0258076 | A1 | 11/2005 | Houzvicka |
| 2006/0116544 | A1 | 6/2006 | Wakui et al. |
| 2009/0321318 | A1 | 12/2009 | Pan et al. |
| 2015/0151283 | A1 * | 6/2015 | Kauffman .............. B01J 23/02 502/213 |
| 2015/0209759 | A1 * | 7/2015 | Al-Hazmi ............ B01J 37/0201 585/660 |
| 2021/0069683 | A1 | 3/2021 | Al-Daous et al. |

OTHER PUBLICATIONS

PCT International Search Report and Written Opinion in International Application No. PCT/US2020/050,115, dated Jan. 12, 2021, 12 pages.

Cortright et al, "L-zeolite-supported platinum and platinum/tin catalysts for isobutane dehydrogenation," Applied Catalysis A: General, vol. 129, issue 1, Aug. 17, 1995, pp. 101-115. 15 pages.

Cortright et al., "Selective dehydrogenation of isobutane over supported Pt/Sn catalysts," Catalysis Today 55, 2000, 11 pages.

Dominguez et al., "Surface and Catalytic Properties of Al2O3—ZRO2 Solid Solutions Prepared by Sol-Gel Methods," Applied Catalysis A: General 197, Issue 1, Apr. 2000, pp. 119-130.

Hill et al., "Silica- and L-zeolite-supported Pt, Pt/Sn and Pt/SN/K catalysts for isobutane dehydrogenation," Applied Catalysis A General vol. 168, Issue 1, Mar. 13, 1998, pp. 9-21, 13 pages.

Klimova et al., "Characterization of Al2O3—ZrO2 mixed oxide catalytic supports prepared by the sol-gel method,"Microporous and Mesoporous Materials, 20, vol. 4-6, Mar. 1998, pp. 293-306.

Larese et al., "Alumina- and Alumina-Zirconia-Supported PTSN Bimetallics: Microstructure and Performance for the N Butane ODH Reaction," Journal of Catalysis 208, Jun. 2002, 2 pages Abstract.

Nazwaz, "Light alkane dehydrogenation to light olefin technologies: A comprehensive review," Review in Chemical Engineering, Aug. 2015, 24 pages.

Resasco, "Dehydrogenation by Hetrogeneous Catalysts," School of Chemical Engineering and Materials Science at University of Oklahoma, Jan. 2000, 52 pages.

Yoldas, "A Transparent Porous Alumina," Amer. Ceram. Soc. Bull., vol. 54, No. 3, (1975), 3 pages.

* cited by examiner

CATALYTIC HYDROCARBON DEHYDROGENATION

TECHNICAL FIELD

This disclosure relates to catalytic dehydrogenation of hydrocarbons.

BACKGROUND

Alkanes are readily available feedstocks from petroleum and gas resources. They are relatively inert in that they exhibit little or no reactivity at conditions typical for activating functional group reactions in organic compounds. A challenge of using alkanes to produce valuable chemicals is the development of economical processes for their selective functionalization. Selective dehydrogenation is a process that converts alkanes (for example, paraffin) into alkenes (for example, olefin), which can be intermediate products in the preparation of useful chemicals such as lubricants, detergent-range alkylaromatics, and alpha olefins.

SUMMARY

This disclosure describes technologies relating to catalytic dehydrogenation of hydrocarbons, and more specifically to selective catalytic dehydrogenation of hydrocarbons including 3 to 6 carbon atoms (for example, C3-C6 alkanes). The subject matter described in this disclosure can be implemented in particular implementations, so as to realize one or more of the following advantages. First, the catalysts described in this disclosure are selective in dehydrogenating normal alkanes to their corresponding linear alkenes or dienes. Second, the catalysts described in this disclosure can inhibit skeletal isomerization and cracking side reactions due to the modification of acidity of the relatively weak acid sites on the gamma-alumina through the impregnation of zirconium and alkali metal. Third, the catalysts described in this disclosure exhibit additional stability against processes comprising a steaming process, thereby allowing the use of steam in a diluent gas in the hydrocarbon stream. Fourth, the addition of small amounts of hydrogen to the diluent gas can enhance the activity in dehydrogenation of C3-C6 alkanes, increase the selectivity for linear alkenes and dienes in the product, and improve the stability of the catalysts described in this disclosure.

Certain aspects of the subject matter described can be implemented as a catalyst for dehydrogenation of hydrocarbons. The catalyst includes a support including zirconium oxide and alumina. A concentration of the zirconium oxide in the catalyst is in a range of from 1 weight percent (wt. %) to 20 wt. %. The catalyst includes from 0.01 wt. % to 2 wt. % of an alkali metal or alkaline earth metal. The catalyst includes from 1 wt. % to 2 wt. % of tin. The catalyst includes from 0.1 wt. % to 2 wt. % of a platinum group metal. The alkali metal or alkaline earth metal, tin, and platinum group metal are disposed on the support.

This, and other aspects, can include one or more of the following features.

The alkali metal or alkaline earth metal can be selected from the group consisting of lithium, sodium, potassium, rubidium, cesium, beryllium, magnesium, calcium, and barium.

The alkali metal can be potassium or cesium.

The alumina can include gamma-alumina or theta-alumina.

The platinum group metal can be selected from the group consisting of platinum, ruthenium, iridium, rhodium, and palladium.

The catalyst can be configured to dehydrogenate hydrocarbons including 3 to 6 carbon atoms at an operating temperature in a range of from about 500 degrees Celsius (° C.) to about 800° C. and an operating pressure in a range of from about 0.01 bar to about 10 bar.

The catalyst can be configured to dehydrogenate hydrocarbons including 3 to 6 carbon atoms in the presence of a diluent gas including hydrogen, steam, inert gas, or combinations thereof.

A concentration of hydrogen in the diluent gas can be in a range of from 5 volume percent (vol. %) to 30 vol. %.

Certain aspects of the subject matter described can be implemented as a method of dehydrogenating hydrocarbons. The hydrocarbons to be dehydrogenated are subjected to an operating temperature in a range of from about 500° C. to about 800° C. within a reactor. The hydrocarbons to be dehydrogenated are subjected to an operating pressure in a range of from about 0.01 bar to about 10 bar within the reactor. While subjecting the hydrocarbons to the operating temperature and operating pressure within the reactor, a diluent gas is introduced within the reactor. The diluent gas includes hydrogen, steam, inert gas, or combinations of these. While subjecting the hydrocarbons to the operating temperature and operating pressure within the reactor, a catalyst disposed within the reactor is used to dehydrogenate the hydrocarbons in the presence of the diluent gas within the reactor. The catalyst includes a support including zirconium oxide and alumina. A concentration of the zirconium oxide in the catalyst is in a range of from 1 wt. % to 20 wt. %. The catalyst includes from 0.01 wt. % to 2 wt. % of an alkali metal or alkaline earth metal. The catalyst includes from 1 wt. % to 2 wt. % of tin. The catalyst includes from 0.1 wt. % to 2 wt. % of a platinum group metal. The alkali metal or alkaline earth metal, tin, and platinum group metal are disposed on the support.

This, and other aspects, can include one or more of the following features.

The alkali metal or alkaline earth metal can be selected from the group consisting of lithium, sodium, potassium, rubidium, cesium, beryllium, magnesium, calcium, and barium.

The alkali metal can be potassium or cesium.

The alumina can include gamma-alumina or theta-alumina.

A concentration of hydrogen in the diluent gas can be in a range of from 5 vol. % to 30 vol. %.

Before using the catalyst to dehydrogenate the hydrocarbons, the catalyst can be activated. The catalyst can be reduced to form catalyst grains with diameters in a range of from 200 micrometers to 500 micrometers. The catalyst grains can be placed within the reactor. A stream including oxygen can be flowed to the catalyst grains within the reactor. While flowing the stream including oxygen to the catalyst grains, a temperature within the reactor can be increased to 450° C. After the temperature within the reactor reaches 450° C., a stream including an inert gas can be flowed to the catalyst grains within the reactor. While flowing the stream including the inert gas to the catalyst grains, the temperature within the reactor can be decreased to 400° C. After the temperature within the reactor reaches 400° C., a stream including hydrogen can be flowed to the catalyst grains within the reactor. The temperature within the reactor can be adjusted to the operating temperature.

Certain aspects of the subject matter described can be implemented as a method of preparing a catalyst for dehydrogenation of hydrocarbons. An alumina is mixed with an aqueous solution of a first additive to form a first slurry. The first additive includes a salt or complex including zirconium. The first slurry is dried to form a first solid. The first solid is mixed with an aqueous solution of a second additive to form a second slurry. The second additive includes a salt including an alkali metal or an alkaline earth metal. The second slurry is dried in the presence of oxygen to form a second solid. In some implementations, the second slurry is dried and further heated in the presence of oxygen to form the second solid. The second solid is mixed with an ethanolic solution of a third additive to form a third slurry. The third additive includes a salt or complex including tin. The third slurry is dried to form a third solid. The third solid is mixed with an aqueous solution of a fourth additive to form a fourth slurry. The fourth additive includes a salt or complex including a platinum group metal. The fourth slurry is dried to form the catalyst. The catalyst includes from 1 wt. % to 20 wt. % of zirconia derived from the first additive. The catalyst includes from 0.01 wt. % to 2 wt. % of the alkali metal or alkaline earth metal derived from the second additive. The catalyst includes from 1 wt. % to 2 wt. % of the tin derived from the third additive. The catalyst includes from 0.1 wt. % to 2 wt. % of the platinum group metal derived from the fourth additive. The catalyst includes a balance of the alumina.

This, and other aspects, can include one or more of the following features.

The first additive can be selected from the group consisting of zirconium oxynitrate, zirconium oxychloride, zirconium acetate, and zirconium acetylacetonate.

An anionic portion of the salt in the second additive can be selected from the group consisting of nitrate ion, nitrite ion, sulfate ion, hydroxide ion, and halide ion.

The third additive can be selected from the group consisting of tin(II) chloride dihydrate, tin(IV) chloride hydrate, and tin(IV) bis(acetylacetonate).

The fourth additive can be selected from the group consisting of dihydrogen hexachloroplatinate hexahydrate, tetraammineplatinum dihydroxide, tetraammineplatinum dinitrate, and tetraammineplatinum dichloride.

The alumina can be gamma-alumina or theta-alumina.

The gamma-alumina can be formed. Alumina (for example, boehmite alumina) can be dispersed in water. Nitric acid can be added to the dispersion of alumina in water to form a first particulate sol. The first particulate sol can be mixed under reflux to form a second particulate sol. A liquid phase of the second particulate sol can be optically clear. The second particulate sol can be freeze-dried to form a dried solid. The dried solid can be heated in the presence of oxygen to form the gamma-alumina. The formed gamma-alumina can have a Brunauer-Emmett-Teller (BET) surface area of at least 200 square meters per gram.

The details of one or more implementations of the subject matter of this disclosure are set forth in the accompanying drawings and the description. Other features, aspects, and advantages of the subject matter will become apparent from the description, the drawings, and the claims.

DETAILED DESCRIPTION

This disclosure describes catalytic dehydrogenation of hydrocarbons. A preferable dehydrogenation catalyst satisfies at least three requirements, namely high activity, high selectivity, and good stability. Activity is a measure of the catalyst's ability to convert reactants into products at specified temperature, pressure, contact time and presence of diluents such as hydrogen, steam, nitrogen or a combination of them, if any. Selectivity is a measure of the amount of desired species (such as olefins) in the product (for example, in mole percent) relative to the total moles of the hydrocarbons converted. Stability is a measure of the rate of change with time of the activity and selectivity parameters. Catalysts with slower rates of change are considered to be more stable. For example, a catalyst with high stability may exhibit no change in activity rate during a desired reaction time duration, such as a couple days.

Alkane dehydrogenation reactions are endothermic and are generally favored by high temperature and low hydrogen pressure. These conditions can also potentially lead to cracking side reactions, isomerization, and accelerated loss of catalytic activity due deactivation. For the selective dehydrogenation processes described in this disclosure, it is desirable to dehydrogenate normal hydrocarbon feedstock to produce linear alkenes with little or no simultaneous cracking or isomerization reactions, which can tend to produce smaller and/or branched hydrocarbon chains, respectively. Preferably, the isomerization or cracking activity of the selective dehydrogenation catalysts are maintained at less than 3-5 mole percent (mol. %) of the feedstock, measured as the number of moles of isomerized or cracked hydrocarbons in the product relative to the feedstock.

Figure 1:
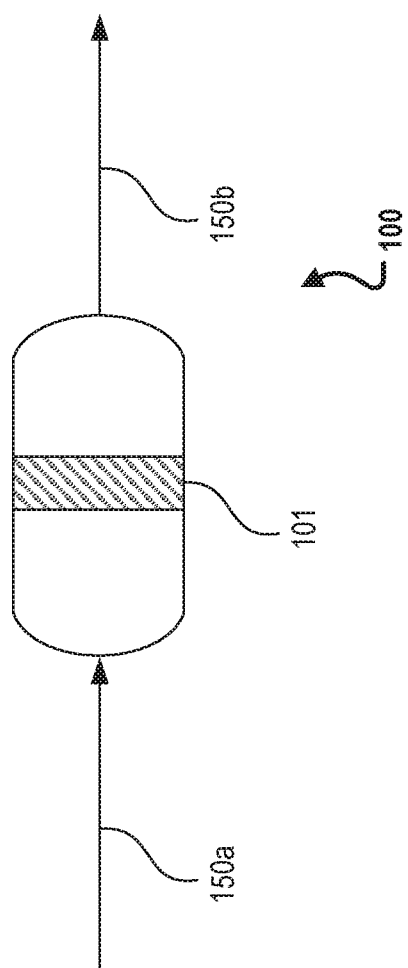
FIG. 1 is a schematic diagram of an example reactor for catalytic hydrocarbon dehydrogenation.

FIG. 1 is a schematic diagram of an example reactor 100 for catalytic hydrocarbon dehydrogenation. The reactor 100 can be, for example, a fixed bed reactor or a fluidized bed reactor. Although shown in FIG. 1 as a horizontal reactor, in some implementations the reactor 100 is a vertical reactor. A feed stream 150a is introduced to the reactor 100. The feed stream 150a can include various species, for example, hydrocarbons (such as C3-C6 alkanes), a diluent gas, or combinations of these. The diluent gas can include hydrogen ($H_2$), steam ($H_2O$), methane ($CH_4$), inert gas (such as nitrogen ($N_2$) and argon), or any combination of these. A reaction can occur within the reactor 100, thereby converting one or more species from the feed stream 150a into one or more other species. For example, at least a portion of the hydrocarbons from the feed stream 150a can be dehydrogenated to form one or more alkenes, dienes, or a combination of both. The effluent 150b includes the reaction products (such as alkenes) and any unreacted species from the feed stream 150a (such as inert gas and alkanes that did not react within the reactor 100).

The rate of reactions occurring within the reactor 100 can depend on the operating conditions within the reactor 100. The operating conditions within the reactor 100 can be adjusted in order to adjust the rate of reactions occurring within the reactor 100. In some implementations, the reactor 100 includes a heater, which can be used to adjust the temperature within the reactor 100. In some implementations, the feed stream 150a is heated to a desired temperature before it is introduced to the reactor 100, and in such cases, it may not be necessary for the reactor 100 to include a heater. In some implementations, the reactor 100 is equipped with one or more sensors, such as one or more pressure sensors, one or more temperature sensors, or combinations of these. The one or more sensors can be used to monitor one or more operating conditions (such as temperature and/or pressure) within the reactor 100.

A catalyst 101 is disposed within the reactor 100. The presence of the catalyst 101 can increase the rate of reactions within the reactor 100. The catalyst 101 includes a support that is crystalline and includes a solid mixture of zirconium oxide ($ZrO_2$ and referred also as zirconia) and alumina ($Al_2O_3$). The support is loaded with an alkali metal or alkaline earth metal. Tin and a platinum group metal are also disposed on the support. The catalyst 101 can be used to dehydrogenate hydrocarbons, such as hydrocarbons including 3 to 10 carbon atoms. The catalyst 101 is selective in dehydrogenating normal alkanes to their corresponding linear alkenes or dienes. The catalyst 101 can be selective in dehydrogenating C3-C6 alkanes (that is, propane, butane, pentane, and hexane) over alkanes including fewer or more carbon atoms.

In some implementations for conversion of n-butane, the catalyst 101 exhibits a large selectivity for linear butenes (for example, 1-butene, cis-2-butene, trans-2-butene) in a range of from about 78 mol. % to about 93 mol. %. In some implementations for conversion of n-butane, the catalyst 101 exhibits a large selectivity for linear butenes that is greater than about 90 mol. %. In some implementations for conversion of n-butane, the catalyst 101 exhibits a selectivity for butadiene (also known as 1,3-butadiene) in a range of from about 3 mol. % to about 7 mol. %. In some implementations for conversion of n-butane, the catalyst 101 exhibits a selectivity for butadiene that is less than about 5 mol. %. In some implementations for conversion of n-butane, the catalyst 101 exhibits a small selectivity for branched butene (also known as isobutylene) in a range of from about 0.1 mol. % to about 2 mol. %. In some implementations for conversion of n-butane, the catalyst 101 exhibits a small selectivity for branched butene that is less than about 0.5 mol. %.

In some implementations for conversion of n-pentane, the catalyst 101 exhibits a large selectivity for linear pentenes (for example, 1-pentene, cis-2-pentene, trans-2-pentene) in a range of from about 39 mol. % to about 73 mol. %. In some implementations for conversion of n-pentane, the catalyst 101 exhibits a large selectivity for linear pentenes that is greater than about 70 mol. %. In some implementations for conversion of n-pentane, the catalyst 101 exhibits a selectivity for pentadienes (for example, 1,4-pentadiene, (Z)-1,3-pentadiene, (E)-1,3-pentadiene) in a range of from about 13 mol. % to about 24 mol. %. In some implementations for conversion of n-pentane, the catalyst 101 exhibits a selectivity for pentadienes that is less than about 13 mol. %. In some implementations for conversion of n-pentane, the catalyst 101 exhibits a small selectivity for branched pentenes (for example, 3-methyl-1-butene, 2-methyl-1-butene, 2-methyl-2-butene) in a range of from about 2 mol. % to about 13 mol. %. In some implementations for conversion of n-pentane, the catalyst 101 exhibits a small selectivity for branched pentenes that is less than about 3 mol. %.

A concentration of zirconia in the catalyst 101 can be adjusted based on a desired characteristic of the catalyst 101. For example, the concentration of zirconia in the catalyst 101 can be adjusted based on a desired acidity of the catalyst 101. The acidity of the catalyst 101 can affect the selectivity of the catalyst 101 for one or more products. The concentration of zirconia in the catalyst 101 is in a range of from 1 weight percent (wt. %) to 20 wt. %. For example, the concentration of zirconia in the catalyst 101 is in a range of from 5 wt. % to 15 wt. %. The catalyst 101 including such concentrations of zirconia can be effective in butane and pentane dehydrogenation. For example, the catalyst 101 having a concentration of zirconia that is about 20 wt. % can be effective in butane dehydrogenation. For example, the catalyst 101 having a concentration of zirconia that is about 10 wt. % can be effective in pentane dehydrogenation.

The alkali metal can be, for example, lithium, sodium, potassium, rubidium, or cesium. The alkaline earth metal can be, for example, beryllium, magnesium, calcium, or barium. The alkali metal or alkaline earth metal can neutralize the acidity of the catalyst 101. A concentration of alkali metal or alkaline earth metal in the catalyst 101 can be adjusted based on a desired characteristic of the catalyst 101. For example, the concentration of alkali metal or alkaline earth metal in the catalyst 101 can be adjusted based on a desired neutralization of acidity of the catalyst 101. As mentioned before, the acidity of the catalyst 101 can affect the selectivity of the catalyst 101 for one or more products. The concentration of zirconia and alkali metal (or alkaline earth metal) can be adjusted according to the desired acidity of the catalyst 101. The concentration of alkali metal or alkaline earth metal in the catalyst 101 is in a range of from 0.01 wt. % to 3 wt. %. For example, the concentration of alkali metal or alkaline earth metal in the catalyst 101 is in a range of from 1.5 wt. % to 2 wt. %.

The presence of tin in the catalyst 101 can modify its catalytic activity. The tin can interact with the platinum group metal in the catalyst 101. For example, the tin can contact the surface of platinum group metal particles. Platinum group metals can, in some cases, be responsible for undesired side reactions (resulting in undesired products), and the tin contacting such platinum group metal particles can render such particles inactive, allowing the catalyst 101 to be more selective towards desired products. A concentration of tin in the catalyst 101 is in a range of from 1 wt. % to 2 wt. %. For example, the concentration of tin in the catalyst 101 is in a range of from 1.2 wt. % to 1.5 wt. %.

The platinum group metal can be, for example, platinum, ruthenium, iridium, rhodium, or palladium. A concentration of platinum group metal in the catalyst 101 is in a range of from 0.1 wt. % to 2 wt. %. For example, the concentration of platinum group metal in the catalyst 101 is in a range of from 0.5 wt. % to 1 wt. %. In some implementations, a molar ratio of tin to platinum in the catalyst 101 is in a range of about 3:1 to about 5:1.

A balance of the catalyst 101 (that is, the remaining portion of the catalyst 101 excluding the zirconia, alkali metal or alkaline earth metal, tin, and platinum group metal) is alumina. In some implementations, a concentration of alumina in the catalyst is in a range of from 70 wt. % to 98 wt. %. For example, the concentration of alumina in the catalyst 101 is in a range of from 73 wt. % to 98 wt. %. For example, the concentration of alumina in the catalyst 101 is in a range of from 80 wt. % to 97 wt. %. The alumina can be gamma-alumina or theta-alumina. It is preferable for the alumina in the catalyst 101 to have a Brunauer-Emmett-Teller (BET) surface area of at least 200 square meters per gram ($m^2/g$). In some implementations, the alumina in the catalyst 101 has a BET surface area in a range of from 200 $m^2/g$ to 300 $m^2/g$.

Figure 2:
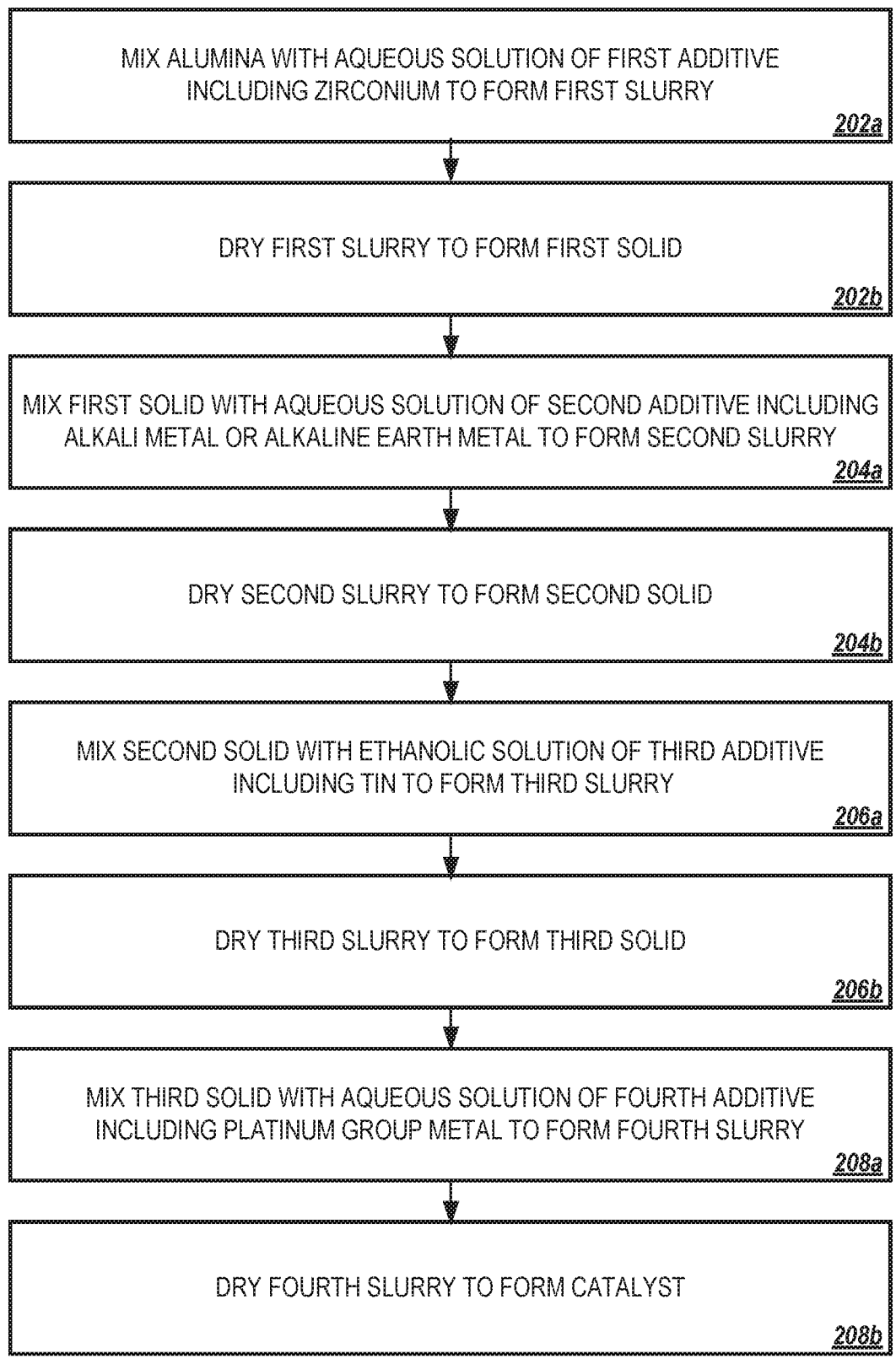
FIG. 2 is a flow chart of an example method for preparing a catalyst for hydrocarbon dehydrogenation.

FIG. 2 is a flow chart of an example method 200 for preparing a catalyst (for example, the catalyst 101) for hydrocarbon dehydrogenation. The method 200 can include one or more techniques for preparing the catalyst 101. For example, the method 200 can include catalyst impregnation (such as pore-volume wetness impregnation), precipitation, ion-exchange, gelation, or any combination of these techniques.

At step 202a, an alumina is mixed with an aqueous solution of a first additive to form a first slurry. The first additive includes a salt (or complex) that includes zirconium. For example, the first additive can be zirconium oxynitrate, zirconium oxychloride, zirconium acetate, or zirconium acetylacetonate. At step 202b, the first slurry is dried to form a first solid. In some implementations, the first slurry is dried at a temperature in a range of from 90° C. to 130° C. For example, the first slurry is dried at 120° C. In some implementations, the first slurry is dried for 12 to 24 hours. For example, the first slurry is dried for 24 hours. In some implementations, the first slurry is dried at 120° C. for 24 hours.

At step 204a, the first solid is mixed with an aqueous solution of a second additive to form a second slurry. The second additive includes a salt including an alkali metal or an alkaline earth metal. An anionic portion of the salt in the second additive can be, for example, a nitrate ion, a nitrite ion, a sulfate ion, a hydroxide ion, or a halide ion (such as a chloride ion). At step 204b, the second slurry is dried and calcined (that is, heated in the presence of oxygen or air) to form a second solid. The second slurry can be dried before calcination at step 204b. In some implementations, the second slurry is dried at a temperature in a range of from 90° C. to 130° C. before calcination. For example, the second slurry is dried at 120° C. before calcination. In some implementations, the second slurry is dried for 12 to 24 hours before calcination. For example, the second slurry is dried for 24 hours before calcination. In some implementations, the second slurry is dried at 120° C. for 24 hours before calcination. The second slurry (now dried) forms the second solid. The second solid can be calcined at step 204b at a temperature in a range of from 550° C. to 650° C. In some implementations, the second solid is calcined at 600° C. The second solid can be calcined at step 204b for 3 to 12 hours. In some implementations, the second solid is calcined for 7 hours. In some implementations, the second solid is calcined at 600° C. for 7 hours.

At step 206a, the second solid is mixed with an ethanolic solution of a third additive to form a third slurry. The third additive includes a salt (or complex) that includes tin. For example, the third additive can be tin(II) chloride dihydrate, tin(IV) chloride hydrate, or tin(IV) bis(acetylacetonate). At step 206b, the third slurry is dried to form a third solid. The third slurry can be dried at step 206b at a temperature in a range of from 85° C. to 110° C. In some implementations, the third slurry is dried at 90° C. The third slurry can be dried at step 206b for 12 to 24 hours. In some implementations, the third slurry is dried for 24 hours. In some implementations, the third slurry is dried at 90° C. for 24 hours.

At step 208a, the third solid is mixed with an aqueous solution of a fourth additive to form a fourth slurry. The fourth additive includes a salt (or complex) that includes a platinum group metal. For example, the fourth additive can be dihydrogen hexachloroplatinate hexahydrate, tetraammineplatinum dihydroxide, tetraammineplatinum dinitrate, or tetraammineplatinum dichloride. At step 208b, the fourth slurry is dried to form the catalyst 101. The fourth slurry can be dried at step 208b at a temperature in a range of from 90° C. to 130° C. In some implementations, the fourth slurry is dried at 120° C. The fourth slurry can be dried at step 208b for 12 to 24 hours. In some implementations, the fourth slurry is dried for 24 hours. In some implementations, the fourth slurry is dried at 120° C. for 24 hours.

In some implementations, the alumina is gamma-alumina or theta-alumina. In some implementations, the method 200 includes forming the gamma-alumina before it is mixed with the aqueous solution of the first additive in step 202a. An alumina (for example, boehmite alumina or pseudoboehmite alumina) can be dispersed in water (for example, deionized water). The dispersion of alumina in water can be stirred and heated for a time period. In some implementations, the dispersion of alumina in water is stirred at 80° C. for 16 to 24 hours. A mineral acid (such as nitric acid) can be added to the dispersion of alumina in water to form a first particulate sol. The mineral acid can be added dropwise. The mineral acid can lower the potential of hydrogen (pH) of the dispersion. In some implementations, the mineral acid lowers the pH of the dispersion to about 2. The first particulate sol can be mixed under reflux to form a second particulate sol. In some implementations, the first particulate sol is mixed for 24 hours under reflux at a temperature in a range of from 100° C. to 135° C. A liquid phase of the second particulate sol can be optically clear. The second particulate sol can be allowed to cool to room temperature. The second particulate sol can be freeze-dried to form a dried solid. The dried solid can be in the form of flakes and/or particles. In some implementations, the second particulate sol is freeze-dried at a liquid nitrogen temperature (for example, −176° C.). The dried solid can be heated in the presence of oxygen to form the gamma-alumina. In some implementations, the dried solid is heated to a temperature in a range of from 475° C. to 700° C. in the presence of static air (which includes oxygen). In some implementations, the dried solid is heated, such that the temperature of the dried solid increases at a rate of 5° C. per minute. For example, the dried solid can be heated to 600° C. at a temperature increase rate of 5° C. per minute under static air. In some implementations, the dried solid is heated for 7 hours under static air. The gamma-alumina can have a BET surface area of at least 200 $m^2/g$. In some implementations, the gamma-alumina has a BET surface area in a range of from 200 $m^2/g$ to 300 $m^2/g$. In some implementations, the gamma-alumina has a BET surface area in a range of from 250 $m^2/g$ to 300 $m^2/g$.

Figure 3:
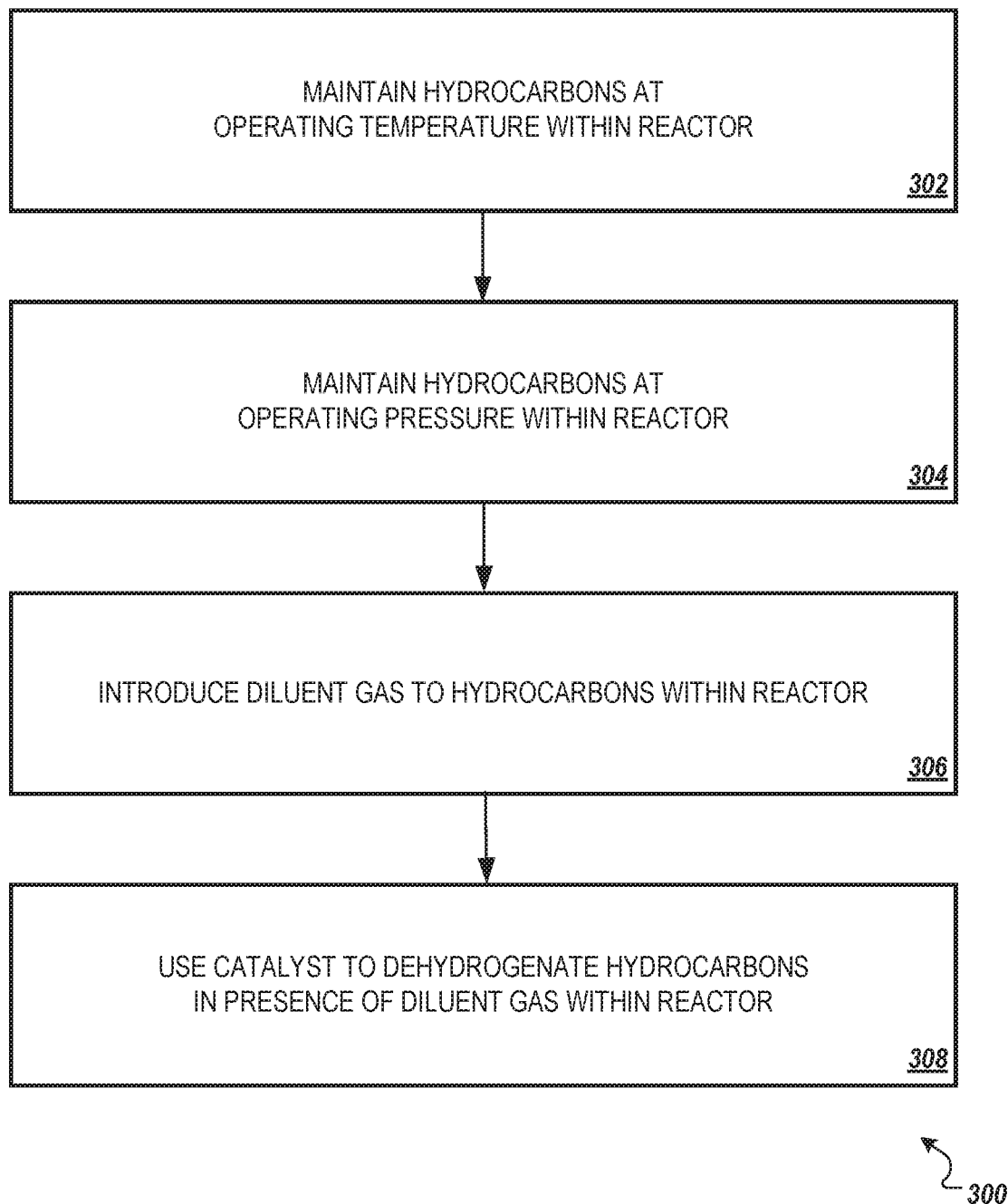
FIG. 3 is a flow chart of an example method for catalytic hydrocarbon dehydrogenation.

FIG. 3 is a flow chart of an example method 300 for catalytic hydrocarbon dehydrogenation. The reactor 100 and the catalyst 101 can be used to implement the method 300. The hydrocarbons to be dehydrogenated can be supplied as a feed stream (150a) to the reactor 100. The hydrocarbons can be supplied as a feed stream 150a to the reactor 100 as a gas phase or a liquid phase.

At step 302, the hydrocarbons to be dehydrogenated are subjected to an operating temperature in a range of from about 500° C. to about 800° C. within the reactor 100. The operating temperature can depend on the composition of the feed stream. For example, the operating temperature for a feed stream including n-butane can be different from the operating temperature for a feed stream including n-pentane (or n-hexane). In some implementations, the operating temperature is in a range of from about 500° C. to about 600° C.

At step 304, the hydrocarbons to be dehydrogenated are subjected to an operating pressure in a range of from about 0.01 bar to about 10 bar within the reactor 100. The operating pressure can depend on the composition of the feed stream. For example, the operating pressure for a feed stream including n-butane can be different from the operating pressure for a feed stream including n-pentane (or n-hexane). In some implementations, the operating pressure is in a range of from about 0.01 bar to about 1 bar. In some implementations, the operating pressure is about 1 bar.

While subjecting the hydrocarbons to the operating temperature and operating pressure within the reactor at steps 302 and 304, respectively, the method progresses to steps 306 and 308. At step 306, a diluent gas is introduced to the hydrocarbons within the reactor 100. As mentioned previously, the diluent gas can include hydrogen, steam, methane, inert gas (such as nitrogen and argon), or any combination of these. In some implementations, a concentration of hydrogen in the diluent gas is in a range of from 5 volume percent (vol. %) to 30 vol. %. In some implementations, the concentration of hydrogen in the diluent gas is in a range of from 5 vol. % to 20 vol. %. In some implementations, the diluent gas is a portion of the feed stream 150a being supplied to the reactor 100 (that is, the diluent gas and the hydrocarbons are supplied to the reactor 100 together). In some implementations, the diluent gas is supplied to the reactor 100 separate from the feed stream 150a. At step 308, the catalyst 101 disposed within the reactor 100 is used to dehydrogenate the hydrocarbons in the presence of the diluent gas within the reactor 100.

In some implementations, the catalyst 101 is activated before it is used to dehydrogenate the hydrocarbons at step 308. Catalyst 101 activation occurs before step 302. The catalyst 101 can be reduced to form catalyst grains with diameters in a range of from 200 micrometers to 500 micrometers. The catalyst grains can be placed within the reactor 100. A stream including oxygen (for example, air) can be flowed to the catalyst grains within the reactor 101. While flowing the stream including oxygen to the catalyst grains, the temperature within the reactor can be increased to greater than 400° C. (for example, 450° C. or greater). Heating the catalyst 101 in the presence of oxygen can result in conversion of tin and platinum group metal ions into their respective solid oxides as well as remove any undesired organic residue, volatile residue, or both from the catalyst 101. In some implementations, the temperature is increased at a temperature increase rate of 1.5° C. per minute. After the temperature within the reactor 100 is greater than 400° C., that temperature can be maintained for a time duration (for example, at least 4 hours). Then a stream including an inert gas (such as nitrogen or argon) can be flowed to the catalyst grains within the reactor 100. The inert gas is used to purge the oxygen from the reactor, so that a stream including hydrogen can subsequently be flowed to the catalyst grains. While flowing the stream including the inert gas to the catalyst grains, the temperature within the reactor 100 can be decreased to 400° C. In some implementations, the stream including the inert gas is flowed for 1 hour. Then a stream including hydrogen can be flowed to the catalyst grains within the reactor 100. The introduction of hydrogen to the catalyst 101 can result in conversion of tin and platinum group metal oxides into a metallic mixture, which can then be considered the catalytically active state of the tin-platinum mixture in the catalyst 101. The stream including hydrogen can be flowed for 4 to 7 hours. In some implementations, the stream including hydrogen is flowed for 4 hours. At this point, the catalyst 101 has been activated. The temperature within the reactor 100 can then be adjusted to the desired operating temperature for hydrocarbon dehydrogenation. Step 302 can then be implemented.

EXAMPLES

Example 1: Gamma-Alumina Preparation

Gamma-alumina was synthesized by peptizing commercial pseudoboehmite alumina dispersion in water with a mineral acid to yield a stable particulate sol. 60 grams of CATAPAL®-200 alumina boehmite (trademark of SASOL) was dispersed in 350 grams of deionized water. The dispersion was stirred at 80° C. for 16-24 hours. 2-3 milliliters of concentrated (84-86%) nitric acid ($HNO_3$) was added dropwise to lower the pH of the dispersion to about 2. The dispersion was stirred under reflux (at 100° C.-135° C.) for 24 hours to form a particulate sol. The particulate sol was allowed to cool to room temperature before freeze-drying at liquid nitrogen temperature (−176° C.) to form dried flakes. The dried flakes were heated at a temperature increase rate of 5° C. per minute until 600° C. was reached, and then the dried flakes were maintained at 600° C. for 7 hours under static air to produce the gamma-alumina. The final product was gamma-alumina with a BET surface area in a range of from 250 $m^2/g$ to 300 $m^2/g$. This gamma-alumina was used in the preparation of each of the catalysts in Examples 2-12 (Catalysts A-K).

Example 2: Catalyst A Preparation 10.0 grams of gamma-alumina was loaded with 5 wt. % zirconia. The method used was pore-volume wetness impregnation where 2.29 grams of zirconium acetate solution (17 wt. % Zr) was diluted with deionized water to a total volume of 20 milliliters. The zirconium acetate solution was added to the solid alumina, mixed until a homogenous paste was obtained, and dried at 120° C. for 24 hours.

10.0 grams of the dried zirconia-alumina powder was loaded with 1.5 wt. % potassium by pore-volume wetness impregnation. 4.45 milliliter of 0.875 molar potassium hydroxide (KOH) aqueous solution was diluted with deionized water to a total volume of 15 milliliters. The solution was added to the solid zirconia-alumina, mixed until a homogenous paste was obtained, and dried at 120° C. for 24 hours. The dried sample was calcined at 600° C. for 7 hours in air.

10.0 grams of the calcined zirconia-alumina was loaded with 1.36 wt. % tin by pore-volume wetness impregnation. 9.68 milliliter of 0.12 molar tin chloride ($SnCl_2.2H_2O$) ethanolic solution was added to the solid, mixed until a homogenous paste was obtained, and dried at 90° C. for 24 hours. 10.0 grams of the dried solid was then loaded with 0.75 wt. % platinum (Pt) by adding 10.0 milliliter of 0.039 molar chloroplatinic acid hexahydrate ($H_2PtCl_6.6H_2O$) aqueous solution to the solid powder, mixed until a homogenous paste was obtained, and dried at 120° C. for 24 hours.

Example 3: Catalyst B Preparation 10.0 grams of gamma-alumina was loaded with 5 wt. % zirconia. The method used was pore-volume wetness impregnation where 2.29 grams of zirconium acetate solution (17 wt. % Zr) was diluted with deionized water to a total volume of 20 milliliters. The zirconium acetate solution was added to the solid alumina, mixed until a homogenous paste was obtained, and dried at 120° C. for 24 hours.

10.0 grams of the dried zirconia-alumina powder was loaded with 1.75 wt. % potassium by pore-volume wetness impregnation. 5.21 milliliter of 0.875 molar potassium hydroxide (KOH) aqueous solution was diluted with deionized water to a total volume of 15 milliliters. The solution was added to the solid zirconia-alumina, mixed until a homogenous paste was obtained, and dried at 120° C. for 24 hours. The dried sample was calcined at 600° C. for 7 hours in air.

10.0 grams of the calcined zirconia-alumina was loaded with 1.36 wt. % tin by pore-volume wetness impregnation. 9.68 milliliter of 0.12 molar tin chloride ($SnCl_2.2H_2O$) ethanolic solution was added to the solid, mixed until a homogenous paste was obtained, and dried at 90° C. for 24 hours. 10.0 grams of the dried solid was then loaded with 0.75 wt. % platinum (Pt) by adding 10.0 milliliter of 0.039 molar chloroplatinic acid hexahydrate ($H_2PtCl_6.6H_2O$) aqueous solution to the solid powder, mixed until a homogenous paste was obtained, and dried at 120° C. for 24 hours.

Example 4: Catalyst C Preparation 10.0 grams of gamma-alumina was loaded with 5 wt. % zirconia. The method used was pore-volume wetness impregnation where 2.29 grams of zirconium acetate solution (17 wt. % Zr) was diluted with deionized water to a total volume of 20 milliliters. The zirconium acetate solution was added to the solid alumina, mixed until a homogenous paste was obtained, and dried at 120° C. for 24 hours.

10.0 grams of the dried zirconia-alumina powder was loaded with 2.0 wt. % potassium by pore-volume wetness impregnation. 5.97 milliliter of 0.875 molar potassium hydroxide (KOH) aqueous solution was diluted with deionized water to a total volume of 15 milliliters. The solution was added to the solid zirconia-alumina, mixed until a homogenous paste was obtained, and dried at 120° C. for 24 hours. The dried sample was calcined at 600° C. for 7 hours in air.

10.0 grams of the calcined zirconia-alumina was loaded with 1.36 wt. % tin by pore-volume wetness impregnation. 9.68 milliliter of 0.12 molar tin chloride ($SnCl_2.2H_2O$) ethanolic solution was added to the solid, mixed until a homogenous paste was obtained, and dried at 90° C. for 24 hours. 10.0 grams of the dried solid was then loaded with 0.75 wt. % platinum (Pt) by adding 10.0 milliliter of 0.039 molar chloroplatinic acid hexahydrate ($H_2PtCl_6.6H_2O$) aqueous solution to the solid powder, mixed until a homogenous paste was obtained, and dried at 120° C. for 24 hours.

Example 5: Catalyst D Preparation 10.0 grams of gamma-alumina was loaded with 10 wt. % zirconia. The method used was pore-volume wetness impregnation where 4.84 grams of zirconium acetate solution (17 wt. % Zr) was diluted with deionized water to a total volume of 20 milliliters. The zirconium acetate solution was added to the solid alumina, mixed until a homogenous paste was obtained, and dried at 120° C. for 24 hours.

10.0 grams of the dried zirconia-alumina powder was loaded with 1.5 wt. % potassium by pore-volume wetness impregnation. 4.45 milliliter of 0.875 molar potassium hydroxide (KOH) aqueous solution was diluted with deionized water to a total volume of 15 milliliters. The solution was added to the solid zirconia-alumina, mixed until a homogenous paste was obtained, and dried at 120° C. for 24 hours. The dried sample was calcined at 600° C. for 7 hours in air.

10.0 grams of the calcined zirconia-alumina was loaded with 1.36 wt. % tin by pore-volume wetness impregnation. 9.68 milliliter of 0.12 molar tin chloride ($SnCl_2.2H_2O$) ethanolic solution was added to the solid, mixed until a homogenous paste was obtained, and dried at 90° C. for 24 hours. 10.0 grams of the dried solid was then loaded with 0.75 wt. % platinum (Pt) by adding 10.0 milliliter of 0.039 molar chloroplatinic acid hexahydrate ($H_2PtCl_6.6H_2O$) aqueous solution to the solid powder, mixed until a homogenous paste was obtained, and dried at 120° C. for 24 hours.

Example 6: Catalyst E Preparation 10.0 grams of gamma-alumina was loaded with 10 wt. % zirconia. The method used was pore-volume wetness impregnation where 4.84 grams of zirconium acetate solution (17 wt. % Zr) was diluted with deionized water to a total volume of 20 milliliters. The zirconium acetate solution was added to the solid alumina, mixed until a homogenous paste was obtained, and dried at 120° C. for 24 hours.

10.0 grams of the dried zirconia-alumina powder was loaded with 1.75 wt. % potassium by pore-volume wetness impregnation. 5.21 milliliter of 0.875 molar potassium hydroxide (KOH) aqueous solution was diluted with deionized water to a total volume of 15 milliliters. The solution was added to the solid zirconia-alumina, mixed until a homogenous paste was obtained, and dried at 120° C. for 24 hours. The dried sample was calcined at 600° C. for 7 hours in air.

10.0 grams of the calcined zirconia-alumina was loaded with 1.36 wt. % tin by pore-volume wetness impregnation. 9.68 milliliter of 0.12 molar tin chloride ($SnCl_2.2H_2O$) ethanolic solution was added to the solid, mixed until a homogenous paste was obtained, and dried at 90° C. for 24 hours. 10.0 grams of the dried solid was then loaded with 0.75 wt. % platinum (Pt) by adding 10.0 milliliter of 0.039 molar chloroplatinic acid hexahydrate ($H_2PtCl_6.6H_2O$) aqueous solution to the solid powder, mixed until a homogenous paste was obtained, and dried at 120° C. for 24 hours.

Example 7: Catalyst F Preparation 10.0 grams of gamma-alumina was loaded with 10 wt. % zirconia. The method used was pore-volume wetness impregnation where 4.84 grams of zirconium acetate solution (17 wt. % Zr) was diluted with deionized water to a total volume of 20 milliliters. The zirconium acetate solution was added to the solid alumina, mixed until a homogenous paste was obtained, and dried at 120° C. for 24 hours.

10.0 grams of the dried zirconia-alumina powder was loaded with 2.0 wt. % potassium by pore-volume wetness impregnation. 5.97 milliliter of 0.875 molar potassium hydroxide (KOH) aqueous solution was diluted with deionized water to a total volume of 15 milliliters. The solution was added to the solid zirconia-alumina, mixed until a homogenous paste was obtained, and dried at 120° C. for 24 hours. The dried sample was calcined at 600° C. for 7 hours in air.

10.0 grams of the calcined zirconia-alumina was loaded with 1.36 wt. % tin by pore-volume wetness impregnation. 9.68 milliliter of 0.12 molar tin chloride ($SnCl_2.2H_2O$) ethanolic solution was added to the solid, mixed until a homogenous paste was obtained, and dried at 90° C. for 24 hours. 10.0 grams of the dried solid was then loaded with 0.75 wt. % platinum (Pt) by adding 10.0 milliliter of 0.039 molar chloroplatinic acid hexahydrate ($H_2PtCl_6.6H_2O$) aqueous solution to the solid powder, mixed until a homogenous paste was obtained, and dried at 120° C. for 24 hours.

Example 8: Catalyst G Preparation 10.0 grams of gamma-alumina was loaded with 15 wt. % zirconia. The method used was pore-volume wetness impregnation where 7.68 grams of zirconium acetate solution (17 wt. % Zr) was diluted with deionized water to a total volume of 20 milliliters. The zirconium solution was added to the solid alumina, mixed until a homogenous paste was obtained, and dried at 120° C. for 24 hours.

10.0 grams of the dried zirconia-alumina powder was loaded with 1.5 wt. % potassium by pore-volume wetness impregnation. 4.45 milliliter of 0.875 molar potassium hydroxide (KOH) aqueous solution was diluted with deionized water to a total volume of 15 milliliters. The solution was added to the solid zirconia-alumina, mixed until a homogenous paste was obtained, and dried at 120° C. for 24 hours. The dried sample was calcined at 600° C. for 7 hours in air.

10.0 grams of the calcined zirconia-alumina was loaded with 1.36 wt. % tin by pore-volume wetness impregnation. 9.68 milliliter of 0.12 molar tin chloride ($SnCl_2 \cdot 2H_2O$) ethanolic solution was added to the solid, mixed until a homogenous paste was obtained, and dried at 90° C. for 24 hours. 10.0 grams of the dried solid was then loaded with 0.75 wt. % platinum (Pt) by adding 10.0 milliliter of 0.039 molar chloroplatinic acid hexahydrate ($H_2PtCl_6 \cdot 6H_2O$) aqueous solution to the solid powder, mixed until a homogenous paste was obtained, and dried at 120° C. for 24 hours.

Example 9: Catalyst H Preparation 10.0 grams of gamma-alumina was loaded with 15 wt. % zirconia. The method used was pore-volume wetness impregnation where 7.68 grams of zirconium acetate solution (17 wt. % Zr) was diluted with deionized water to a total volume of 20 milliliters. The zirconium acetate solution was added to the solid alumina, mixed until a homogenous paste was obtained, and dried at 120° C. for 24 hours.

10.0 grams of the dried zirconia-alumina powder was loaded with 1.75 wt. % potassium by pore-volume wetness impregnation. 5.21 milliliter of 0.875 molar potassium hydroxide (KOH) aqueous solution was diluted with deionized water to a total volume of 15 milliliters. The solution was added to the solid zirconia-alumina, mixed until a homogenous paste was obtained, and dried at 120° C. for 24 hours. The dried sample was calcined at 600° C. for 7 hours in air.

10.0 grams of the calcined zirconia-alumina was loaded with 1.36 wt. % tin by pore-volume wetness impregnation. 9.68 milliliter of 0.12 molar tin chloride ($SnCl_2 \cdot 2H_2O$) ethanolic solution was added to the solid, mixed until a homogenous paste was obtained, and dried at 90° C. for 24 hours. 10.0 grams of the dried solid was then loaded with 0.75 wt. % platinum (Pt) by adding 10.0 milliliter of 0.039 molar chloroplatinic acid hexahydrate ($H_2PtCl_6 \cdot 6H_2O$) aqueous solution to the solid powder, mixed until a homogenous paste was obtained, and dried at 120° C. for 24 hours.

Example 10: Catalyst I Preparation 10.0 grams of gamma-alumina was loaded with 15 wt. % zirconia. The method used was pore-volume wetness impregnation where 7.68 grams of zirconium acetate solution (17 wt. % Zr) was diluted with deionized water to a total volume of 20 milliliters. The zirconium acetate solution was added to the solid alumina, mixed until a homogenous paste was obtained, and dried at 120° C. for 24 hours.

10.0 grams of the dried zirconia-alumina powder was loaded with 2.0 wt. % potassium by pore-volume wetness impregnation. 5.97 milliliter of 0.875 molar potassium hydroxide (KOH) aqueous solution was diluted with deionized water to a total volume of 15 milliliters. The solution was added to the solid zirconia-alumina, mixed until a homogenous paste was obtained, and dried at 120° C. for 24 hours. The dried sample was calcined at 600° C. for 7 hours in air.

10.0 grams of the calcined zirconia-alumina was loaded with 1.36 wt. % tin by pore-volume wetness impregnation. 9.68 milliliter of 0.12 molar tin chloride ($SnCl_2 \cdot 2H_2O$) ethanolic solution was added to the solid, mixed until a homogenous paste was obtained, and dried at 90° C. for 24 hours. 10.0 grams of the dried solid was then loaded with 0.75 wt. % platinum (Pt) by adding 10.0 milliliter of 0.039 molar chloroplatinic acid hexahydrate ($H_2PtCl_6 \cdot 6H_2O$) aqueous solution to the solid powder, mixed until a homogenous paste was obtained, and dried at 120° C. for 24 hours.

Example 11: Catalyst J Preparation 10.0 grams of gamma-alumina was loaded with 20 wt. % zirconia. The method used was pore-volume wetness impregnation where 10.89 grams of zirconium acetate solution (17 wt. % Zr) was diluted with deionized water to a total volume of 20 milliliters. The zirconium acetate solution was added to the solid alumina, mixed until a homogenous paste was obtained, and dried at 120° C. for 24 hours.

10.0 grams of the dried zirconia-alumina powder was loaded with 1.5 wt. % potassium by pore-volume wetness impregnation. 4.45 milliliter of 0.875 molar potassium hydroxide (KOH) aqueous solution was diluted with deionized water to a total volume of 15 milliliters. The solution was added to the solid zirconia-alumina, mixed until a homogenous paste was obtained, and dried at 120° C. for 24 hours. The dried sample was calcined at 600° C. for 7 hours in air.

10.0 grams of the calcined zirconia-alumina was loaded with 1.36 wt. % tin by pore-volume wetness impregnation. 9.68 milliliter of 0.12 molar tin chloride ($SnCl_2 \cdot 2H_2O$) ethanolic solution was added to the solid, mixed until a homogenous paste was obtained, and dried at 90° C. for 24 hours. 10.0 grams of the dried solid was then loaded with 0.75 wt. % platinum (Pt) by adding 10.0 milliliter of 0.039 molar chloroplatinic acid hexahydrate ($H_2PtCl_6 \cdot 6H_2O$) aqueous solution to the solid powder, mixed until a homogenous paste was obtained, and dried at 120° C. for 24 hours.

Example 12: Catalyst K Preparation

Catalyst K was free of zirconia and prepared as a control for comparison. 10.0 grams of gamma-alumina was loaded with 1.5 wt. % potassium by pore-volume wetness impregnation. 4.45 milliliter of 0.875 molar potassium hydroxide (KOH) aqueous solution was diluted with deionized water to a total volume of 15 milliliters. The solution was added to the solid alumina, mixed until a homogenous paste was obtained, and dried at 120° C. for 24 hours. The dried sample was calcined at 600° C. for 7 hours in air.

10.0 grams of the calcined gamma-alumina was loaded with 1.36 wt. % tin by pore-volume wetness impregnation. 9.68 milliliter of 0.12 molar tin chloride ($SnCl_2 \cdot 2H_2O$) ethanolic solution was added to the solid, mixed until a homogenous paste was obtained, and dried at 90° C. for 24 hours. 10.0 grams of the dried solid was then loaded with 0.75 wt. % platinum (Pt) by adding 10.0 milliliter of 0.039 molar chloroplatinic acid hexahydrate ($H_2PtCl_6 \cdot 6H_2O$) aqueous solution to the solid powder, mixed until a homogenous paste was obtained, and dried at 120° C. for 24 hours.

Table 1 lists the weight concentrations of various components in each of the catalysts described in the previous examples. The balance of each of the catalysts was the gamma-alumina.

TABLE 1

Catalyst compositions

| Catalyst | $ZrO_2$ (wt. %) | Potassium (wt. %) | Platinum (wt. %) | Tin (wt. %) |
|---|---|---|---|---|
| A | 5 | 1.5 | 0.75 | 1.36 |
| B | 5 | 1.75 | 0.75 | 1.36 |
| C | 5 | 2 | 0.75 | 1.36 |
| D | 10 | 1.5 | 0.75 | 1.36 |
| E | 10 | 1.75 | 0.75 | 1.36 |
| F | 10 | 2 | 0.75 | 1.36 |
| G | 15 | 1.5 | 0.75 | 1.36 |
| H | 15 | 1.75 | 0.75 | 1.36 |
| I | 15 | 2 | 0.75 | 1.36 |
| J | 20 | 1.5 | 0.75 | 1.36 |
| K | 0 | 1.5 | 0.75 | 1.36 |

Example 13: Catalyst Activation

Each of the catalysts were activated in a reactor before hydrocarbon dehydrogenation testing. For each of the catalysts, the following procedure was performed. 8 tonnes of pressure were applied to form catalyst grains with diameters in a range of from 200 micrometers to 500 micrometers. 0.75 grams (about 1.5 cubic centimeters) of the catalyst grains were packed into a tubular Hastelloy-X reactor having a length of 310 millimeters and an internal diameter of 9.1 millimeters. The reactor included a thermocouple immersed in the catalyst bed for adjusting the reactor temperature to a desired operating temperature. Air was flowed to the catalyst bed within the reactor at a rate of 100 cubic centimeters per minute. While air was flowed, the temperature within the reactor was increased to 450° C. at a temperature increase rate of 1.5° C. per minute. Once the temperature reached 450° C., the temperature was maintained at 450° C. for at least 4 hours. The catalyst bed was then purged with nitrogen at a rate of 100 cubic centimeters per minute for 1 hour while the temperature within the reactor was decreased to 400° C. Hydrogen was then flowed to the catalyst bed within the reactor at a rate of 100 cubic centimeters per minute for 4 hours. The temperature within the reactor was then increased to the reaction temperature of the respective test (525° C. for n-pentane dehydrogenation and 550° C. for n-butane dehydrogenation, which are described in more detail in Examples 14 and 15, respectively) at a temperature increase rate of 2° C. per minute.

Example 14: Normal Pentane Dehydrogenation

Figure 4:
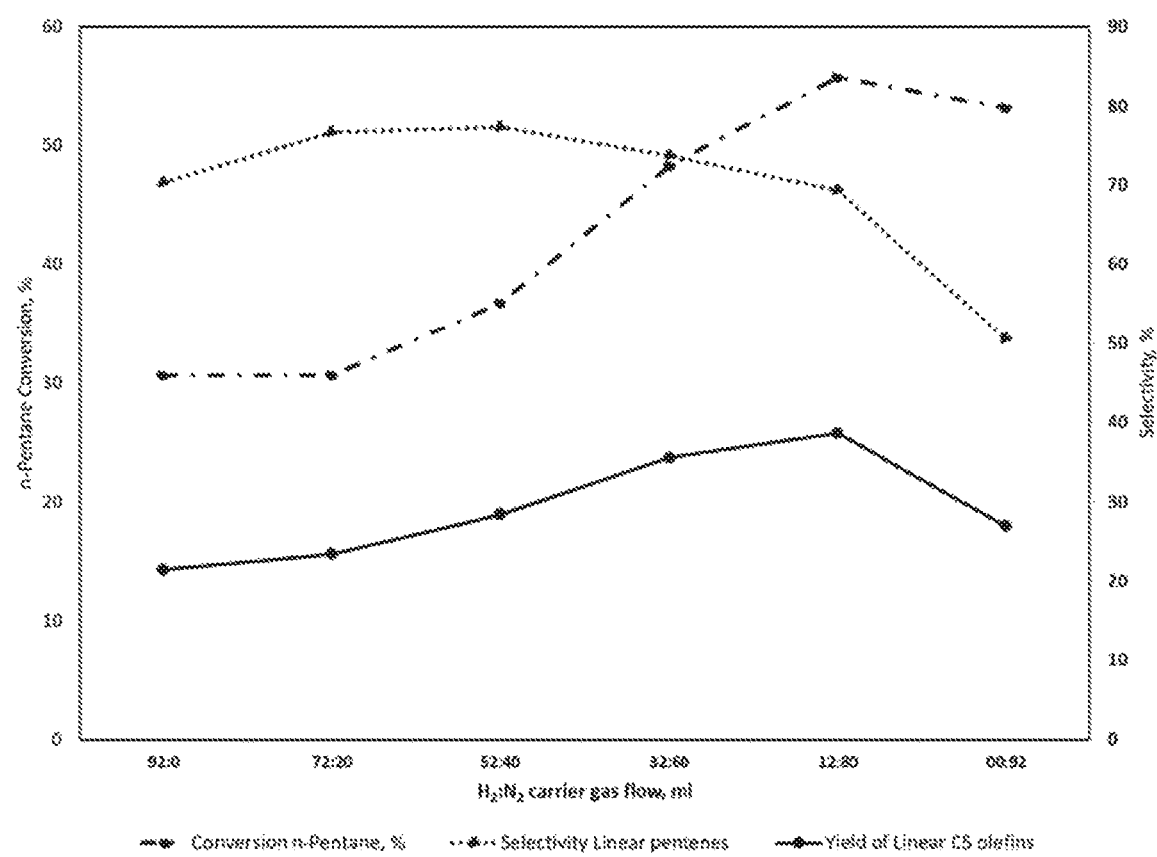
FIG. 4 is a graph showing results of n-pentane dehydrogenation for various diluent gas compositions using an example catalyst.

Catalysts A, B, C, D, F, G, H, I, and K were tested for dehydrogenation of n-pentane in a fixed bed reactor. Each of the catalysts (0.75 grams each) were tested for 8 hours on stream at 525° C. under atmospheric pressure, which reflects the relatively high stability of these catalysts. A feed of liquid n-pentane was supplied at a rate of 0.04 milliliters per minute (mL/min), such that the weight hourly space velocity was 2 per hour. The diluent gas used for each of the tests was a mixture of hydrogen ($H_2$) and nitrogen ($N_2$). The diluent gas was provided at a flow rate of 92.24 mL/min. For each of the catalysts, the ratio of hydrogen to nitrogen in the diluent gas was varied as follows: 92.24 mL/min of $H_2$ and 0 mL/min of $N_2$ (pure hydrogen); 82.24 mL/min of $H_2$ and 10 mL/min of $N_2$; 72.24 mL/min of $H_2$ and 20 mL/min of $N_2$; 62.24 mL/min of $H_2$ and 30 mL/min of $N_2$; 52.24 mL/min of $H_2$ and 40 mL/min of $N_2$; 42.24 mL/min of $H_2$ and 50 mL/min of $N_2$; 32.24 mL/min of $H_2$ and 60 mL/min of $N_2$; 22.24 mL/min of $H_2$ and 70 mL/min of $N_2$; 12.24 mL/min of $H_2$ and 80 mL/min of $N_2$; and 0 mL/min of $H_2$ and 92.24 mL/min of $N_2$ (pure nitrogen). It was found that a ratio of 12.54:79.7 of $H_2$:$N_2$ in the diluent gas provided maximum yields of the desired product (n-pentenes), and the results corresponding to this ratio are provided in Table 2. FIG. 4 also shows a comparison of n-pentane conversion, linear pentene selectivity, and linear olefin yield for various ratios of hydrogen to nitrogen in the diluent gas for Catalyst D.

TABLE 2

Normal pentane dehydrogenation with optimal $H_2$:$N_2$ ratio in diluent gas

| Catalyst | $ZrO_2$ (wt. %) | K (M)[a] | Conversion (mol. %)[b] | Selectivity (mol. %) | | | Yield (mol. %)[c] |
| | | | | Linear pentene[c] | pentadiene[d] | Branched pentene[e] | |
|---|---|---|---|---|---|---|---|
| A | 5 | 1.5 | 73.9 | 38.8 | 13.5 | 10.6 | 28.7 |
| B | 5 | 1.75 | 60.3 | 64.3 | 20.9 | 3.5 | 38.8 |
| C | 5 | 2.0 | 52.6 | 70.8 | 23.3 | 2.2 | 37.5 |
| D | 10 | 1.5 | 62.3 | 64.7 | 27.7 | 2.8 | 40.3 |
| F | 10 | 2.0 | 55.8 | 69.3 | 23.9 | 2.9 | 38.7 |
| G | 15 | 1.5 | 63.0 | 40.2 | 16.4 | 19.6 | 25.3 |
| H | 15 | 1.75 | 55.2 | 55.6 | 22.4 | 4.5 | 30.7 |
| I | 15 | 2.0 | 42.6 | 71.8 | 16.1 | 2.6 | 30.6 |
| K | 0 | 1.5 | 77.6 | 36.8 | 13.1 | 12.8 | 28.6 |

[a]molar concentration of potassium aqueous solution
[b]n-pentane conversion
[c]1-pentene, cis-2-pentene, trans-2-pentene
[d]1,4-pentadiene, (Z)-1,3-pentadiene, (E)-1,3-pentadiene
[e]3-methyl-1-butene, 2-methyl-1-butene, 2-methyl-2-butene As shown in Table 2, although control Catalyst K (zirconia-free) exhibited the greatest dehydrogenation activity (conversion of n-pentane), it also exhibited relatively high hydroisomerization and isomerization activity (producing isopentane and branched pentenes). In contrast, n-pentane conversion for zirconia-containing catalysts (Catalysts A through I) resulted in greater combined selectivity for normal pentenes and pentadienes in comparison to control Catalyst K. Furthermore, for catalysts containing 5-10 wt. % zirconia (Catalysts A through F), yield for normal pentenes reached a maximum of 40.3 mol. % and a minimum of less than 3 mol. % selectivity for branched pentenes.

Example 15: Normal Butane Dehydrogenation

Catalysts A, D, G, J, and K were tested for dehydrogenation of n-butane in a fixed bed reactor. Each of the catalysts (0.75 grams each) were tested for 10 hours on stream at 550° C. under atmospheric pressure, which reflects the relatively high stability of these catalysts. A feed of pressurized liquid n-butane was supplied at a rate of 0.0261 mL/min, such that the weight hourly space velocity was 1 per hour. The diluent gas used for each of the tests was a mixture of hydrogen ($H_2$) and steam ($H_2O$). The diluent gas was provided at a flow rate of 94.83 mL/min. For each of the catalysts, the ratio of hydrogen to steam in the diluent gas was varied as follows: 10 mL/min of $H_2$ and 84.83 mL/min of $H_2O$; 7.5 mL/min of $H_2$ and 85.33 mL/min of $H_2O$; 5 mL/min of $H_2$ and 89.83 mL/min of $H_2O$; 2.5 mL/min of $H_2$ and 90.33 mL/min of $H_2O$; and 0 mL/min of $H_2$ and 94.83 mL/min of $H_2O$ (pure steam). It was found that a ratio of 7.5:87.3 of $H_2$:$H_2O$ in the diluent gas provided maximum yields of the desired product (linear butenes), and the results corresponding to this ratio are provided in Table 3.

TABLE 3

Normal butane dehydrogenation with optimal $H_2$:$H_2O$ in diluent gas

| Catalyst | $ZrO_2$ (wt. %) | K $(M)^a$ | Conversion (mol. %)$^b$ | Selectivity (mol. %) | | | Yield (mol. %) |
| --- | --- | --- | --- | --- | --- | --- | --- |
| | | | | Linear butene$^c$ | 1,3-butadiene | Isobutylene | |
| A | 5 | 1.5 | 45.2 | 91.9 | 3.3 | 0.4 | 41.5 |
| D | 10 | 1.5 | 46.4 | 91.2 | 5.7 | 0.2 | 42.3 |
| G | 15 | 1.5 | 50.4 | 89.8 | 6.0 | 0.1 | 45.3 |
| J | 20 | 1.5 | 71.1 | 86.0 | 6.8 | 0.8 | 61.1 |
| K | 0 | 1.5 | 76.8 | 77.8 | 6.1 | 1.4 | 59.8 |

$^a$molar concentration of treated potassium metal in aqueous solution
$^b$n-butane conversion
$^c$1-butene, cis-2-butene, trans-2-butene As shown in Table 3, for increasing amounts of zirconia in the catalyst: the conversion of n-butane increased; the selectivity for linear butenes decreased; and selectivity for 1,3-butadiene increased. Catalyst J (20 wt. % zirconia content) exhibited a greater yield of linear butenes and a lesser selectivity for isobutylene in comparison to control Catalyst K (zirconia-free).

In this disclosure, the terms "a," "an," or "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed in this disclosure, and not otherwise defined, is for the purpose of description only and not of limitation. Any use of section headings is intended to aid reading of the document and is not to be interpreted as limiting; information that is relevant to a section heading may occur within or outside of that particular section.

In this disclosure, "approximately" means a deviation or allowance of up to 10 percent (%) and any variation from a mentioned value is within the tolerance limits of any machinery used to manufacture the part. Likewise, "about" can also allow for a degree of variability in a value or range, for example, within 10%, within 5%, or within 1% of a stated value or of a stated limit of a range.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "0.1% to about 5%" or "0.1% to 5%" should be interpreted to include about 0.1% to about 5%, as well as the individual values (for example, 1%, 2%, 3%, and 4%) and the sub-ranges (for example, 0.1% to 0.5%, 1.1% to 2.2%, 3.3% to 4.4%) within the indicated range. The statement "X to Y" has the same meaning as "about X to about Y," unless indicated otherwise. Likewise, the statement "X, Y, or Z" has the same meaning as "about X, about Y, or about Z," unless indicated otherwise.

While this disclosure contains many specific implementation details, these should not be construed as limitations on the subject matter or on what may be claimed, but rather as descriptions of features that may be specific to particular implementations. Certain features that are described in this disclosure in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Nevertheless, it will be understood that various modifications, substitutions, and alterations may be made. While operations are depicted in the drawings or claims in a particular order, this should not be understood as requiring that such operations be performed in the particular order shown or in sequential order, or that all illustrated operations be performed (some operations may be considered optional), to achieve desirable results. Accordingly, the previously described example implementations do not define or constrain this disclosure.

What is claimed is:

1. A catalyst for dehydrogenation of hydrocarbons, the catalyst comprising:
    a support comprising zirconium oxide and alumina, wherein a concentration of the zirconium oxide in the catalyst is in a range of from 5 weight percent (wt. %) to 15 wt. %;

from 1.5 wt. % to 2 wt. % of potassium disposed on the support;

from 1.2 wt. % to 1.5 wt. % of tin, the tin disposed on the support; and from 0.5 wt. % to 1 wt. % of a platinum group metal, the platinum group metal disposed on the support, wherein the balance is alumina.

2. The catalyst of claim 1, wherein the alumina comprises gamma-alumina or theta-alumina.

3. The catalyst of claim 1, wherein the platinum group metal is selected from the group consisting of platinum, ruthenium, iridium, rhodium, and palladium.

4. The catalyst of claim 1, wherein the catalyst is configured to dehydrogenate hydrocarbons including 3 to 6 carbon atoms at an operating temperature in a range of from about 500 degrees Celsius (° C.) to about 800° C. and an operating pressure in a range of from about 0.01 bar to about 10 bar.

5. The catalyst of claim 4, wherein the catalyst is configured to dehydrogenate hydrocarbons including 3 to 6 carbon atoms in the presence of a diluent gas comprising hydrogen, steam, inert gas, or combinations thereof.

6. The catalyst of claim 5, wherein a concentration of hydrogen in the diluent gas is in a range of from 5 volume percent (vol. %) to 30 vol. %.

7. The catalyst of claim 1, wherein the catalyst comprises from 1.5 wt. % to 1.75 wt % potassium.

8. The catalyst of claim 7, wherein the catalyst comprises from 10 wt. % to 15 wt. % zirconium oxide.

9. The catalyst of claim 1, wherein the catalyst comprises from 10 wt. % to 15 wt. % zirconium oxide.

10. The catalyst of claim 1, wherein the catalyst comprises 1.5 wt. % potassium.

11. The catalyst of claim 1, wherein the catalyst comprises 1.75 wt. % potassium.

12. The catalyst of claim 1, wherein the catalyst comprises from 2 wt. % potassium.

13. The catalyst of claim 1, wherein the catalyst comprises 5 wt. % zirconium oxide.

14. The catalyst of claim 1, wherein the catalyst comprises 10 wt. % zirconium oxide.

15. The catalyst of claim 1, wherein the catalyst comprises 20 wt. % zirconium oxide.

16. The catalyst of claim 1, wherein the catalyst comprises 10 wt % zirconium oxide and 1.5 wt % potassium.

17. The catalyst of claim 1, wherein the catalyst comprises 10 wt % zirconium oxide and 2 wt % potassium.

18. The catalyst of claim 1, wherein the catalyst comprises 5 wt % zirconium oxide and 2 wt % potassium.

19. The catalyst of claim 1, wherein the catalyst comprises 5 wt % zirconium oxide and 1.75 wt % potassium.

20. The catalyst of claim 1, wherein the catalyst comprises 15 wt % zirconium oxide and 1.75 wt % potassium.

* * * * *

UNITED STATES PATENT AND TRADEMARK OFFICE
CERTIFICATE OF CORRECTION

PATENT NO. : 11,338,269 B2
APPLICATION NO. : 16/566778
DATED : May 24, 2022
INVENTOR(S) : Mohammed Abdulmajeed Al-Daous and Hussam A. Bahlouli It is certified that error appears in the above-identified patent and that said Letters Patent is hereby corrected as shown below:

On the Title Page

Item [72], delete "Thuwa" and insert -- Thuwal --, therefor.

In the Claims

Column 19, Line 26, Claim 7, delete "wt" and insert -- wt. --, therefor.

Column 20, Line 9-10, Claim 12, delete "comprises from" and insert -- comprises --, therefor.

Column 20, Line 18, Claim 16, delete "wt" and insert -- wt. --, therefor.

Column 20, Line 20, Claim 17, delete "wt" and insert -- wt. --, therefor.

Column 20, Line 22, Claim 18, delete "wt" and insert -- wt. --, therefor.

Column 20, Line 24, Claim 19, delete "wt" and insert -- wt. --, therefor.

Column 20, Line 26, Claim 20, delete "wt" and insert -- wt. --, therefor.

Signed and Sealed this
Twelfth Day of July, 2022

Katherine Kelly Vidal
*Director of the United States Patent and Trademark Office*